United States Patent [19]
Watkins et al.

[11] 4,046,000
[45] Sept. 6, 1977

[54] APPARATUS AND METHOD FOR TESTING ARTICLE CARRIERS

[75] Inventors: Richard Kenneth Watkins, Lithonia; William S. Layman, Marietta, both of Ga.

[73] Assignee: The Mead Corporation, Dayton, Ohio

[21] Appl. No.: 772,068

[22] Filed: Feb. 25, 1977

[51] Int. Cl.² ............................................. G01N 3/08
[52] U.S. Cl. ......................................................... 73/95
[58] Field of Search ..................... 73/88 R, 93, 95, 96, 73/97, 102

[56] References Cited
U.S. PATENT DOCUMENTS

| | | | |
|---|---|---|---|
| 1,946,438 | 2/1934 | Drake et al. | 73/95 |
| 2,949,770 | 8/1960 | Kernan et al. | 73/93 |
| 3,724,266 | 4/1973 | Beckstrom | 73/95 |

Primary Examiner—Charles A. Ruehl
Attorney, Agent, or Firm—Walter M. Rodgers; Walter A. Rodgers

[57] ABSTRACT

Loaded article carriers of the basket style are tested by engaging the handle of the carrier with hanger means secured to a suitable gauge mounted on a ram which is driven upwardly by motive means in such manner as to cause the articles to engage a fixedly mounted stop plate and thereby to simulate a gradually increasing load on all critical parts of the carrier the magnitude of which is indicated by the gauge.

13 Claims, 7 Drawing Figures

U.S. Patent  Sept. 6, 1977  4,046,000
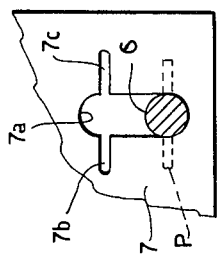
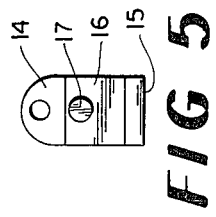
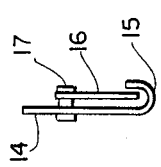
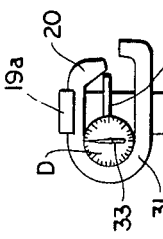
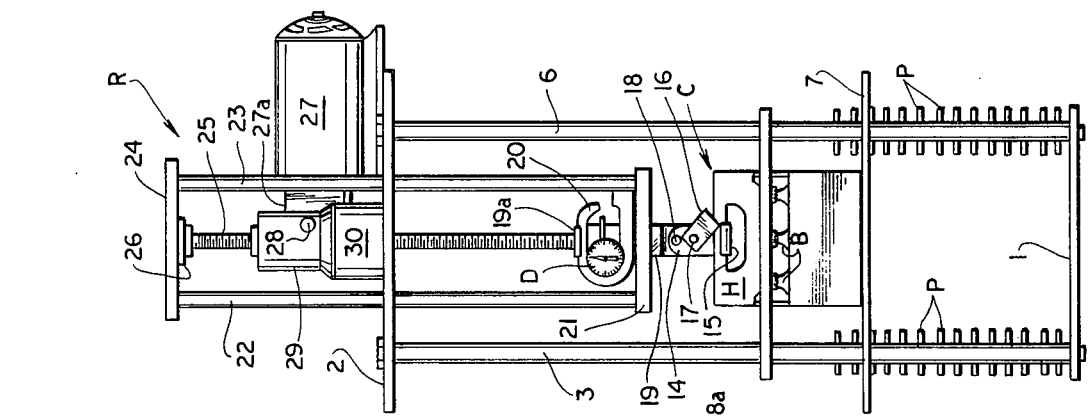
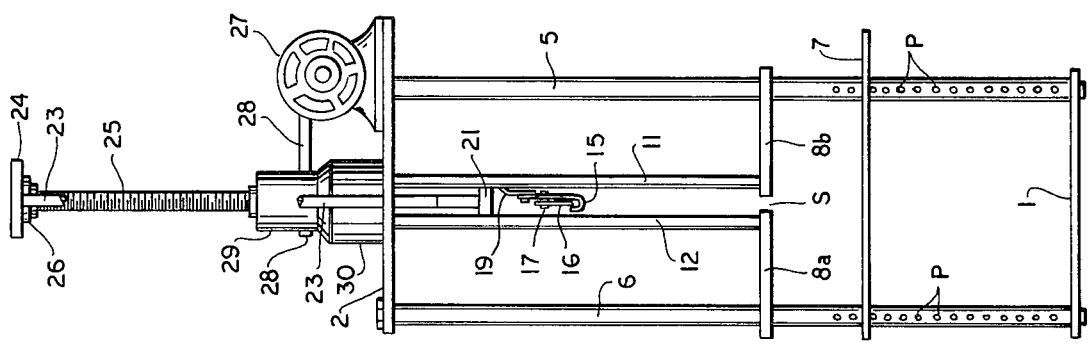
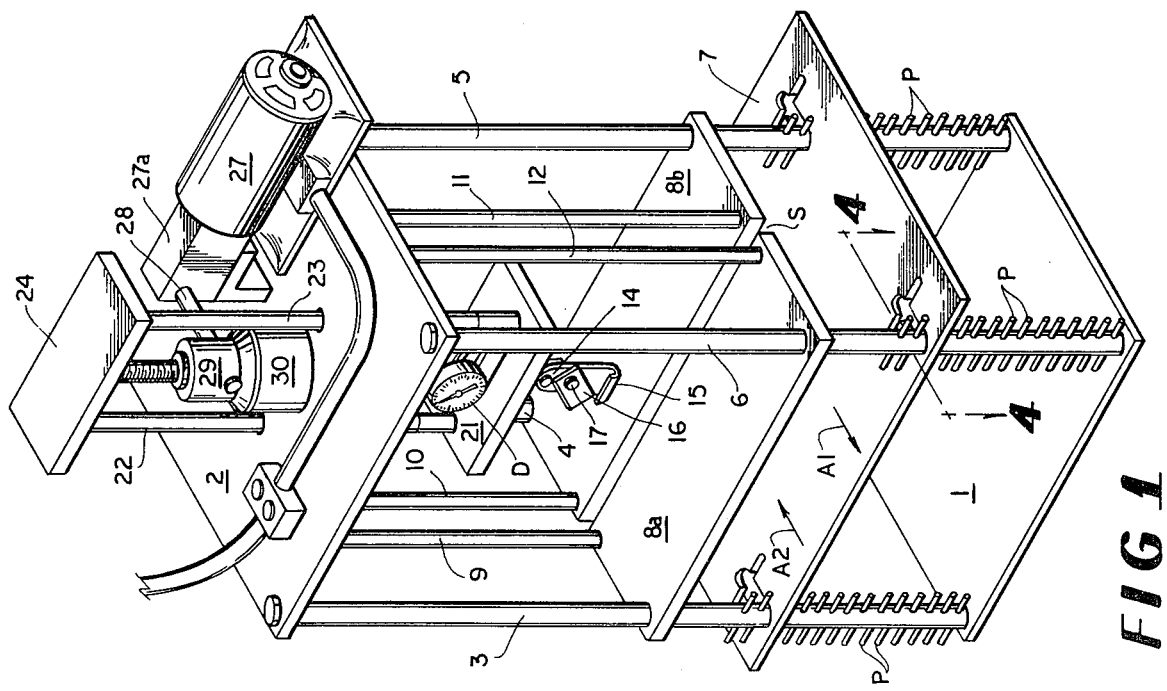

APPARATUS AND METHOD FOR TESTING ARTICLE CARRIERS

The current trend toward larger and larger primary packages such as bottles for soft drinks and the like has resulted in substantial increases in the stresses applied to carriers in which such items are packaged such, for example, as basket style bottle carriers. The use of 32 ounce and 64 ounce bottles not only imposes substantially greater stresses on the carriers in which such large bottles are packaged but the damage which can occur in the event of carrier failure is much greater with the heavier larger bottles.

Currently known testing devices and methods do not closely simulate the actual load stresses imposed on the carriers and furthermore are not conducive to producing uniform results. For example the so-called "jerk" test simply imposes a sudden lifting force on the handle of a loaded carrier. Tests of this type tend to produce erratic results even though great care is taken in the selection of materials and in the manufacturing techniques employed in producing test carriers.

According to this invention, actual loaded stresses imparted to a carrier are closely simulated. By this invention in one form, a loaded basket style article carrier is arranged so that its handle extends through aperture means formed in a stop plate in such manner that the articles loaded within the carrier are disposed below the stop plate and ram structure is movably mounted on the apparatus frame on which the stop plate is mounted in such a way as to impart an upward pull on the handle which results in engagement of the articles in the carrier with the lower surface of the stop plate and the applied force is measured by a gauge which affords an indication of the magnitude of the force required to cause failure of the carrier. The fact that the force is applied through the articles themselves effectively stresses all components of the carton such as the handle, the bottom, the riser panels which interconnect the handle with the end panels, the side glue seams, the side seam score, and the side score line. When failure occurs, the operator notes the magnitude of applied force which caused the failure and also the particular carrier component or components which failed. By this invention it is possible to pinpoint weaknesses and since the method and apparatus closely simulate actual loading conditions, it is possible to obtain reliable test results using a large quantity of a particular carton with a relatively small standard deviation.

For a better understanding of the invention reference may be had to the following detailed description taken in conjunction with the accompanying drawings in which FIG. 1 is a perspective view of testing apparatus constructed according to the invention;

FIG. 2 is a side or end view of the apparatus shown in FIG. 1;

FIG. 3 is a front view of the apparatus shown in FIG. 1;

FIG. 4 is an enlarged fragmentary view taken along the line designated 4—4 in FIG. 1;

FIG. 5 is an enlarged front view of a hanger and its associated keeper by which the carton handle is engaged;

FIG. 6 is an end or side view of the arrangement shown in FIG. 5, and in which

FIG. 7 is an enlarged front view of a gauge which forms an integral part of the mechanism best shown for example in FIGS. 1 and 3.

With reference to the drawing, a frame structure is provided and includes a bottom plate 1, a top plate 2, and corner posts 3, 4, 5 and 6 which are interconnected at the corners of base plate 1 and top plate 2 as is best shown in FIG. 1.

As is best shown in FIGS. 1 and 3, a carrier C to be tested is loaded with packaged articles such as bottles B and is mounted atop catch shelf 7 insuch manner that the handle H of the carrier C extends through a slot or space S between stop plate means 8a and 8b. Of course the stop plate means could be in the form of a single plate with a slot formed therein although the two plate arrangement as shown in the drawings is preferable because it allows a loaded carrier to be inserted atop catch shelf 7 from the side by a sliding action. Stop plate means 8a and 8b is fixedly mounted in place to the corner posts 3, 4, 5 and 6 and the inner edges of the plates adjacent the space S are affixed to vertical supports 9, 10, 11 and 12 as is apparent from FIG. 1. Of course the support posts 9-12 are fixedly secured at their lower ends to the corners of the stop plates 8a and 8b and are rigidly secured at their upper ends to the top plate 2 so that these plates 8a and 8b are fixed in position relative to the frame of the apparatus.

In order to accommodate carriers which are adapted for use in conjunction with bottles of varying height, the catch shelf 7 is adjustably mounted on corner posts 3-6. To this end pins P which are transversely disposed in openings formed in the corner posts serve to support the shelf 7 at different levels. As is best shown in FIG. 4 corner openings, provided at each corner of the shelf 7, are designated at 7a. These openings are oblong as is apparent particularly in FIG. 4 and transverse clearance slots 7b and 7c extend from the side edges of each opening 7a. In order to move the shelf 7 from one location to another, the shelf is moved forwardly in the direction indicated by the arrow A1 to a position in which the associated pin P is aligned with the clearance slots 7b and 7c. When this occurs, it is possible to move the shelf 7 vertically because under these conditions the transverse pins P may pass through the clearance slots 7b and 7c to accommodate vertical movement of shelf 7. When the shelf is moved to the desired level, it is then moved rearwardly in the direction indicated by the arrow A2 to occupy a position such as is represented in FIG. 4 where the pins P are out of registry with slots 7b and 7c and thus afford support for the shelf 7.

For the purpose of imparting an upward force to the handle H of a test carrier such as C, a hanger 14 having an upturned lower end portion 15 is inserted through a conventional finger gripping opening formed within the handle H of carrier C. Hangar 14 is provided with a keeper 16 pivoted at pin 17 to hanger 14. In FIG. 3 the keeper is shown in its side position at which the carrier handle may be mounted on the hanger 14. Following this operation the keeper 16 is swung in a clockwise direction about pin 17 so as securely to grip the handle of the carrier between the keeper 16 and the main body of the hanger 14. Hanger 14 is suspended by pin 18 from a strap 19 the upper transverse end 19a of which overlies a generally C-shaped gauge structure 20.

Gauge structure 20 is movable with ram R and is supported on a cross bar 21 secured to the lower ends of vertically reciprocable rods 22 and 23 which are interconnected at their top ends by a cross bar 24. A threaded element 25 is rigidly affixed to cross bar 24 by means of a mounting pad 26 and is secured against rotation.

For imparting reciprocable vertical movement to the ram R comprising cross bars 21 and 24 and vertical bars 22 and 23, an electric motor 27 is secured by any suitable means to top plate 2 and a gear box 27a driven by motor 27 is arranged to drive a shaft 28. shaft 28 is arranged to operate the elevating mechanism generally designated in the drawings by the numeral 29. Device 29 comprises an outer housing 30 which is fixedly mounted to top plate 2 and an inner sleeve member (not shown) in the drawings but which is internally threaded and cooperates with the external threads of screw 27. The outer surface of the sleeve is provided with teeth which cooperate with a worm gear (not shown) which is securely mounted to shaft 28. Thus operation of motor 27 through gear box 27a and shaft 28 imparts rotary motion to the internal sleeve part within the housing 30 which is fixed against vertical movement relative to the housing. This operation in cooperation with fixed threaded member 25 threadedly related with the internally threaded sleeve causes the ram R to move vertically. Of course vertical movement of the ram structure R imparts vertical movement to gauge 18. If movement of ram R is in an upward direction, tension stress is imparted to strap 19 and to hanger 14 which in turn is applied to the handle H of carrier C. This upward force causes upward movement of the carrier and its associated bottles B at low velocity. When the upper ends of bottles B engage the lower surface of stop plates 8a and 8b, stress is applied to the gauge 18 which can be visually observed on dial D. When the stress becomes sufficient to cause failure of the carrier, the dial indication is noted and recorded along with a designation of the particular component of the carrier which failed. Gauge 20 as is best shown in FIG. 7 simply includes a generally C-shaped structure 31 atop which the part 19a of strap 19 rests. A tension force applied to strap 19 and to the other parts due to upward movement of ram R causes deformation of the C-shaped structure 31. Such deformation is imparted to operating rod 32 which in turn imparts an indicating movement to hand 33 so as to indicate the stress applied in pounds by notations on the indicia of the dial D. Gauge 20 is a conventional structure and one suitable device is known as Dillon force gauge compression model having a 250 pound rating.

The housing 30 and internal parts mounted on the shaft 28 such as the worm gear (not shown) are of conventional construction. One such structure is known as a miniature Jactuator model M-2625-9 manufactured by Duff-Norton Company, Charlotte, NC. In order to establish reliable and uniform standards of carton manufacture, it is customary to prepare under uniform conditions using materials of uniform quality a number of specimen carriers such as 75 carriers and to test each carrier to the point of failure and to record the pounds of force required to effect failure together with the particular component of the carton which failed. Set forth below is a table of actual test data showing the test results of 75 carrier specimens. Each carrier was of 6-bottle capacity and the bottles themselves were 32 ounce returnable bottles. The average force required to cause these cartons to fail was 137.7 pounds with a standard deviation of ten pounds computed by statistical methods. A standard deviation of this magnitude is believed significant for this type of product and for this particular test apparatus and method in that it indicates substantial uniformity and reliability of the test data which are believed attributable in large part to the improved method and apparatus of this invention which closely simulates actual load conditions in actual service:

LEGEND:
H - Handle
B - Bottom
RP - Riser panel
SGS - Side glue seam
SSS - Side seam score
SSL - Side score line

| Sample Number | Force in Pounds | Point of Failure |
|---|---|---|
| 1 | 144 | SSS |
| 2 | 128 | H |
| 3 | 118 | RP |
| 4 | 152 | H & SGS |
| 5 | 130 | H |
| 6 | 142 | H & SGS |
| 7 | 138 | SGS |
| 8 | 146 | H & SGS |
| 9 | 134 | RP |
| 10 | 133 | H |
| 11 | 133 | SGS & SSS |
| 12 | 142 | RP |
| 13 | 143 | RP |
| 14 | 138 | H |
| 15 | 146 | RP |
| 16 | 135 | RP |
| 17 | 145 | H |
| 18 | 143 | RP |
| 19 | 134 | H |
| 20 | 127 | RP |
| 21 | 120 | SGS |
| 22 | 132 | H |
| 23 | 140 | H |
| 24 | 142 | H |
| 25 | 140 | RP |
| 26 | 142 | RP |
| 27 | 145 | RP |
| 28 | 118 | H |
| 29 | 148 | H |
| 30 | 151 | H |
| 31 | 132 | H |
| 32 | 140 | H & SGS |
| 33 | 149 | RP |
| 34 | 130 | H, SSS & SGS |
| 35 | 125 | H |
| 36 | 138 | H & SGS |
| 37 | 140 | H & RP |
| 38 | 138 | RP |
| 39 | 118 | H |
| 40 | 153 | RP |
| 41 | 132 | H |
| 42 | 144 | H |
| 43 | 135 | RP |
| 44 | 166 | H & SGS |
| 45 | 148 | H & SGS |
| 46 | 135 | RP |
| 47 | 152 | RP |
| 48 | 128 | H & SGS |
| 49 | 136 | RP |
| 50 | 120 | H |
| 51 | 144 | H |
| 52 | 128 | RP |
| 53 | 138 | H & RP |
| 54 | 138 | RP |
| 55 | 142 | H |
| 56 | 124 | H & SGS |
| 57 | 139 | H |
| 58 | 148 | H & SGS |
| 59 | 140 | SH |
| 60 | 150 | H & SGS |
| 61 | 135 | H & SGS |
| 62 | 153 | H |
| 63 | 133 | H |
| 64 | 132 | RP |
| 65 | 134 | RP |
| 66 | 138 | RP |
| 67 | 145 | H & SGS |
| 68 | 148 | H & SGS |
| 69 | 133 | H |
| 70 | 139 | RP |
| 71 | 146 | RP |
| 72 | 100 | H |
| 73 | 133 | H |
| 74 | 149 | H |
| 75 | 141 | RP |

The embodiments of the invention in which an exclusive property of privilege is claimed are defined as follows:

1. Apparatus for testing a loaded basket style article carrier having an article receiving basket section depending from a handle section and a plurality of articles disposed in said basket section, said apparatus comprising a frame, stop plate means affixed to said frame and having aperture means for receiving the carrier handle with the carrier basket section and the articles therebelow, ram structure movably mounted on said frame, gauge means mounted on said ram structure, coupling means engageable with the carrier handle and with said gauge means, and motive means arranged to react between said frame and said ram structure and operable to impart relative movement thereto so as to cause the articles in the carrier to engage said stop plate means thereby to impart a simulated gradually increasing loading force to the carrier handle and basket sections the magnitude of which is indicated by said gauge means.

2. Apparatus according to claim 1 wherein a catch shelf is disjointably mounted on said frame structure at a level below said stop plate means for receiving articles dislodged from the carrier following rupture of the carrier.

3. Apparatus according to claim 2 wherein said catch shelf is adjustable vertically.

4. Apparatus according to claim 2 wherein said frame structure comprises a plurality of vertically disposed support posts each having vertically spaced transversely disposed support pins and wherein a plurality of apertures are formed in said catch shelf for receiving said posts respectively, said apertures being configured to accommodate transverse movement of said shelf relative to said posts and also being configured to prevent vertial movement in one direction of said catch shelf relative to said posts when said catch shelf is disposed in one position and to allow vertical movement of said catch shelf relative to said posts when said catch shelf is disposed in a position transverse to said one position.

5. Apparatus according to claim 2 wherein said frame structure comprises a plurality of vertically disposed posts each having vertically spaced transversely disposed support pins and wherein said catch shelf includes apertures for receiving said posts, the apertures being configured to accommodate transverse movement of said catch shelf relative to said posts and also having clearance slots for receiving said support pins thereby to accommodate vertical movement of said catch shelf relative to said posts.

6. Apparatus according to claim 1 wherein said coupling means comprises a downwardly depending hanger of generally J-shaped cross section for engaging a finger gripping aperture formed in the carrier handle.

7. Apparatus according to claim 6 wherein keeper means is mounted on said hanger and engageable with the carrier handle to insure positive engagement between the carrier handle and said hanger.

8. Apparatus according to claim 1 wherein said stop plate means comprises a pair of laterally spaced plates between which the carton handle is slidably inserted.

9. Apparatus for testing a loaded basket style article carrier having an article receiving basket section depending from a handle section and a plurality of articles disposed in said basket section, said apparatus comprising a frame, stop plate means affixed to said frame and having aperture means for receiving the carrier handle with the carrier basket section and the articles therebelow, ram structure movably mounted on said frame, means including coupling means engageable with the carrier handle for interconnecting the carrier handle with said ram structure, and motive means arranged to react between said frame and said ram structure and operable to impart relative movement thereto so as to cause the articles in the carrier to engage said stop plate means thereby to impart a simulated gradually increasing loading force to the carrier handle and basket sections.

10. A method of testing the mechanical strength of a basket style article carrier having bottom, side and end walls and a handle secured to the carrier end walls, the method comprising loading the carrier with articles, restraining the articles in such manner as to prevent movement thereof in a direction away from the carrier bottom wall, imparting a gradually increasing force to the carrier handle in a direction away from the carrier bottom wall until the carrier fails mechanically.

11. A method according to claim 10 wherein the mangitude of applied force is determined at the instant of failure.

12. A method according to claim 10 wherein the precise location and nature of the failure is noted.

13. A method according to claim 10 wherein one or more articles dislodged from the carrier due to failure of the carrier are supported and accumulated immediately adjacent the failed carrier.

* * * * *